(12) United States Patent
Bissinger et al.

(10) Patent No.: US 8,426,490 B2
(45) Date of Patent: Apr. 23, 2013

(54) METHACRYLATE BASED MONOMERS CONTAINING A URETHANE LINKAGE, PROCESS FOR PRODUCTION AND USE THEREOF

(75) Inventors: Peter Bissinger, Diessen (DE); Karsten Dede, Landsberg (DE); Adrian S. Eckert, Herrsching (DE); Marion Kestel, Munich (DE); Christoph Thalacker, Weilheim (DE)

(73) Assignee: 3M Innovative Properties Company, St. Paul, MN (US)

( * ) Notice: Subject to any disclaimer, the term of this patent is extended or adjusted under 35 U.S.C. 154(b) by 243 days.

(21) Appl. No.: 12/679,490

(22) PCT Filed: Sep. 23, 2008

(86) PCT No.: PCT/US2008/077346
§ 371 (c)(1),
(2), (4) Date: Mar. 23, 2010

(87) PCT Pub. No.: WO2009/042574
PCT Pub. Date: Apr. 2, 2009

(65) Prior Publication Data
US 2010/0197824 A1    Aug. 5, 2010

(30) Foreign Application Priority Data
Sep. 26, 2007  (EP) .................................. 07117211

(51) Int. Cl.
*A61K 6/083*  (2006.01)
(52) U.S. Cl.
USPC .......................................... 523/117; 523/116
(58) Field of Classification Search .................... 523/117
See application file for complete search history.

(56) References Cited

U.S. PATENT DOCUMENTS

| | | | |
|---|---|---|---|
| 3,347,954 A | 10/1967 | Bredereck | |
| 3,541,068 A | 11/1970 | Taylor | |
| 3,729,313 A | 4/1973 | Smith | |
| 3,741,769 A | 6/1973 | Smith | |
| 3,808,006 A | 4/1974 | Smith | |
| 4,002,669 A * | 1/1977 | Gross et al. | 560/126 |
| 4,071,424 A | 1/1978 | Dart | |
| 4,250,053 A | 2/1981 | Smith | |
| 4,287,323 A * | 9/1981 | Tefertiller et al. | 522/96 |
| 4,310,688 A * | 1/1982 | Mendoza | 560/222 |
| 4,320,221 A * | 3/1982 | Hoffman | 528/69 |
| 4,394,403 A | 7/1983 | Smith | |
| 4,443,587 A | 4/1984 | Schmitt | |
| 4,544,742 A | 10/1985 | Schmitt | |
| 4,642,126 A | 2/1987 | Zador | |
| 4,648,843 A | 3/1987 | Mitra | |
| 4,652,274 A | 3/1987 | Boettcher | |
| 4,737,593 A | 4/1988 | Ellrich | |
| 4,744,827 A | 5/1988 | Winkel | |
| 4,772,530 A | 9/1988 | Gottschalk | |
| 4,795,823 A | 1/1989 | Schmitt | |
| 4,839,401 A * | 6/1989 | Waknine | 522/14 |
| 4,874,450 A | 10/1989 | Gottschalk | |
| 4,954,414 A | 9/1990 | Adair | |

(Continued)

FOREIGN PATENT DOCUMENTS

| | | |
|---|---|---|
| EP | 0059451 | 9/1982 |
| EP | 0235826 | 9/1987 |

(Continued)

OTHER PUBLICATIONS

Volumne Contraction in photocured dental resins: Dewaele et al.*
ISO 4049 "Dentistry, Polymer-based Filling, Restorative and Luting Materials".
ISO 9917 "Dentistry, Water-based Cements, Part 1: Powder/liquid Acid-base Cements".
Chung, "Correlation Between Degree of Conversion, Filler Concentration and Mechanical Properties of Posterior Composite Resins", J. Oral Rehab., 1990, vol. 17, pp. 487-494.

(Continued)

*Primary Examiner* — James J Seidleck
*Assistant Examiner* — Peter A Salamon
(74) *Attorney, Agent, or Firm* — Stephen L. Crooks

(57) ABSTRACT

The invention relates to a dental composition comprising a monomer or mixture of monomers represented by the following structure

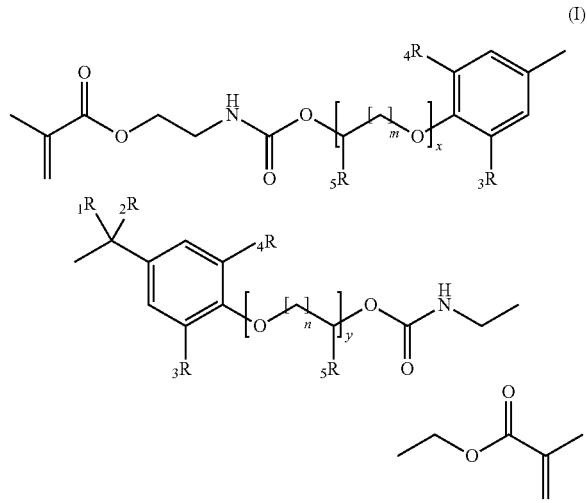

(1) with $_{1,2}R$ independently selected from H, alkyl (e.g. $CH_3C_2H_5$), and Phenyl, $_{3,4}R$ independently selected from H, alkyl (e.g. $CH_3$), and halogen (Cl, Br, F), $_5R$ independently selected from H, alkyl (e.g. $CH_3$), m, n=1, 2 and x+y=2 to 10, with the proviso that if m=n=2, than x+y=2 and if m=n=1, than x+y=4 to 10. The invention also relates to a process for producing the monomer or mixture of monomers and the use thereof especially as dental composition.

10 Claims, No Drawings

U.S. PATENT DOCUMENTS

| | | | |
|---|---|---|---|
| 5,055,372 | A | 10/1991 | Shanklin |
| 5,057,393 | A | 10/1991 | Shanklin |
| 5,332,429 | A | 7/1994 | Mitra |
| 5,484,863 | A | 1/1996 | Molock |
| 5,545,676 | A | 8/1996 | Palazzotto |
| 5,624,260 | A | 4/1997 | Wilcox |
| 5,810,595 | A * | 9/1998 | Mallow ............ 433/228.1 |
| 5,865,803 | A | 2/1999 | Major |
| 5,893,714 | A | 4/1999 | Arnold |
| 5,918,772 | A | 7/1999 | Keller |
| 5,944,419 | A | 8/1999 | Streiff |
| 6,030,606 | A | 2/2000 | Holmes |
| 6,387,981 | B1 * | 5/2002 | Zhang et al. ............ 523/117 |
| 6,572,693 | B1 | 6/2003 | Wu |
| 6,852,775 | B1 | 2/2005 | Soglowek |
| 6,899,948 | B2 | 5/2005 | Zhang |
| 2002/0068771 | A1 * | 6/2002 | Klee et al. ............ 523/115 |
| 2003/0008967 | A1 | 1/2003 | Hecht |
| 2004/0209990 | A1 | 10/2004 | Walz |
| 2005/0070661 | A1 | 3/2005 | Molock |
| 2006/0187752 | A1 | 8/2006 | Keller |
| 2007/0090079 | A1 | 4/2007 | Keller |
| 2007/0172789 | A1 | 7/2007 | Muller |

FOREIGN PATENT DOCUMENTS

| | | |
|---|---|---|
| EP | 0614921 | 9/1994 |
| EP | 614921 A2 * | 9/1994 |
| EP | 0669113 | 8/1995 |
| EP | 1340472 | 9/2003 |
| JP | 2306955 | 12/1990 |
| JP | 05032734 | 2/1993 |
| JP | 06301206 A * | 10/1994 |
| JP | 2001281855 A * | 10/2001 |
| WO | WO 0130304 A1 * | 5/2001 |
| WO | WO 0130306 A1 * | 5/2001 |
| WO | WO 01/95862 | 12/2001 |
| WO | 2005/107626 | 11/2005 |

OTHER PUBLICATIONS

Condon, "In Vitro Wear of Composite with Varied Cure, Filler Level, and Filler Treatment", J. Dent. Res., Jul. 1997, vol. 76, pp. 1405-1411.

Cook, "A Simple Method for the Measurement of Polymerization Shrinkage in dental Composites", Dent. Mater., 1999, vol. 15, pp. 447-449.

Davidson, "The Competition Between the Composite-Dentin Bond Strength and the Polymerization Contraction Stress", J. Dent. Res., Dec. 1984, vol. 63, No. 12, pp. 1396-1399.

De Gee, "True Linear Polymerization Shrinkage of Unfilled Resins and Composites Determined with a Linometer", Dent. Mater., Jan. 1993, vol. 9, pp. 11-14.

Fleming, "Cuspal Movement and Microleakage in Premolar Teeth Restored with Resin-based Filling Materials Cured Using a 'Soft-Start' Polymerisation Protocol", Dent. Mater., 2007, vol. 23, pp. 637-643.

Garcia, "Composite Resins. A Review of the Materials and Clinical Indications", Clinical Dentistry, Med. Oral Patol. Oral Cir. Bucal, 2006, vol. 11, pp. E215-E220.

Garoushi, "Fiber-reinforced Composite Substructure: Load-bearing Capacity of an Onlay Restoration and Flexural Properties of the Material", Journ. Contemp. Dent. Pract., Sep. 2006, vol. 7, No. 4, pp. 1-13.

Ge, "Synthesis and Photopolymerization of Low Shrinkage Methacrylate Monomers Containing Bulky Substituent Groups", Dent. Mater., 2005, vol. 21, pp. 1163-1169.

Guggenberger, "Exploring Beyond Methacrylates", Am. Journ. Dent., Nov. 2000, vol. 13, Special Issue, pp. 82D-84D.

Inan, "Halogenated and Phosphorous Containing Difunctional Monomers for UV-curable Applications", Polymer Preprints, American Chemical Society, Division of Polymer Chemistry, Jan. 1999, vol. 40, No. 1, pp. 47-48. XP008088525.

Inan, "Preparation and Characterization of Novel UV-Curable Urethane Methacrylate and Difunctional Monomers and Their Structure-property Relationships, 1", Macro. Chem. Phys., 2001, vol. 202, pp. 532-540. XP002468576.

Jensen, "Polymerization Shrinkage and Microleakage", International Symposium on Posterior Composite Resin Dental Restorative Materials, Vanherle and Smith, Peter Szulc Publishing Co., 1985, 243-262.

Kim, "A New Resin Matrix for Dental Composite Having Low Volumetric Shrinkage", J. Biomed. Mater. Res., Part B, Appl. Biomater, 2004, vol. 70, pp. 82-90.

Kim, "Characteristics of Novel Dental Composites Containing 2,2-Bis[4-(2-methoxy-3-methacryloyloxy propoxy) phenyl] Propane as a Base Resin", Biomacromolecules, 2006, vol. 7, No. 1, pp. 154-160.

Kim, "Effects of Molecular Structure of the Resins on the Volumetric Shrinkage and the Mechanical Strength of Dental Restorative Composites", Biomacromolecules, 2006, vol. 7, No. 9, pp. 2680-2687.

Meredith, "In Vitro Measurement of Cuspal Strain and Displacement in Composite Restored Teeth", J. Dent., 1997, vol. 25, No. 3-4, pp. 331-337.

Moszner, "New Developments of Polymeric Dental Composites", Prog. Poly. Sci., 2001, vol. 26, pp. 535-576.

Moszner, "Recent Developments of New Components for Dental Adhesives and Composites", Marcomol. Mater. Eng., 2007, vol. 292, p. 245-271.

Munksgaard, "Wall-to-Wall Polymerization Contraction of Composite Resins Versus Filler Content", Scand. J. Dent. Res., Apr., 1987, vol. 95, pp. 526-531.

Okamura, "Development of Dental Composite Resin Utilizing Low-shrinkage and Low-viscous Monomers", Dent. Mater. J. 2006, vol. 25, No. 3, pp. 437-444.

Pallav, "Occlusal Wear Simulation with the ACTA Wear Machine", Occlusal Wear in Dentistry, Fundamental Mechanisms, Clinical Implications, and Laboratory Assessment, Thesis Publishers, Amsterdam, 1996, Chapter 6, p. 63-76.

Pashley, "Clinical Considerations of Microleakage", Journal of Endodontics, Februrary 1990, vol. 16, No. 2, pp. 70-77.

Satsangi, "Synthesis of Low-Shrinkage Polymerizable Liquid-Crystal Monomers", J. Biomed. Mat. Res. B, Appl. Biomat., Jun. 2004, vol. 71B, p. 153-158.

Silikas, "Light Intensity Effects on Resin-Composite Degree of Conversion and Shrinkage Strain", Dent. Mater., 2000, vol. 16, pp. 292-296.

Suliman, "Polymerization Shrinkage of Composite Resins: Comparison With Tooth Deformation", J. Prosthetic Dent., Jan., 1994, vol. 71, pp. 7-12.

Venhoven, "Polymerization Contraction and Conversion of Light-curing BisGMA-based Methacrylate Resins", Biomaterials, 1993, vol. 14, pp. 871-875.

Watts, "Determination of Polymerization Shrinkage Kinetics in Visible-Light-Cured materials: Methods Development", Dent. Mater., Oct. 1991, vol. 7, pp. 281-287.

Weinmann, "Siloranes in Dental Composites", Dent. Mater., 2005, vol. 21, pp. 68-74.

Search Report for EP Application No. 07117211, 10 pages.

Search Report for PCT/US2008/077346, 5 pages.

Written Opinion for PCT/US2008/077346, 7 pages.

* cited by examiner

METHACRYLATE BASED MONOMERS CONTAINING A URETHANE LINKAGE, PROCESS FOR PRODUCTION AND USE THEREOF

CROSS-REFERENCE TO RELATED APPLICATIONS

This application is a national stage filing under 35 U.S.C. 371 of PCT/US2008/077346, filed Sep. 23, 2008, which claims priority to EP Patent Application No. 07117211.8, filed Sep. 26, 2007, the disclosure of which is incorporated by reference in its/their entirety herein.

FIELD OF THE INVENTION

The invention relates to a monomer having a certain formula or a mixture containing the monomer, a process for producing and using this monomer or monomer mixture in the dental field and a dental composition comprising this monomer or monomer mixture.

BACKGROUND ART

In a couple of commercially available dental materials (meth)acrylate based monomers are used.

Sometimes a comparably high molecular weight difunctional (meth)acrylate based monomer like e.g. Bis-GMA is mixed with a comparably low molecular weight (meth)acrylate based co-monomer like e.g. triethyleneglycol dimethacrylate (TEGDMA) having also a comparably low viscosity.

Especially the comparably high molecular weight monomer sometimes shows a structural principle of having a comparably stiff hydrocarbon backbone in the centre of the monomer like e.g. a bisphenol A or a tricyclodecane moiety. (Meth) acrylate functional groups are attached to this backbone as (meth)acrylic acid esters via an aliphatic chain that may contain hetero atoms like e.g. oxygen. These materials typically show on average a volume shrinkage of about 2.0 to about 3.5 vol-% during curing determined according to the Archimedes buoyancy principle, DIN 13907 correlated with Linometer measurements (cf. Am. J. Dent. 2000, 13 (special issue), 82D-84D and Dent. Mater. 1993, 9, 11-14).

High volume shrinkage during curing might cause unwanted and/or detrimental side-effects like e.g. enamel fracture, cracked cusps, and cuspal movement as well as failures of the composite-tooth interface and thus, should be reduced. On the other hand dental compositions should have sufficient mechanical properties.

In order to maintain a high level of mechanical properties of the cured composition but also to reduce the volume shrinkage during curing, different approaches have been suggested.

One typical approach is to raise the amount of inorganic filler. This, however, may cause a lower degree of conversion during curing of the (meth)acrylate groups because of the reduced amount of organic resin present.

Another approach is to increase the molecular weight of the monomers. In this respect, using pre-polymeric (meth) acrylate functional urethanes based on bisphenol derivatives have been suggested.

A further approach is to use a mixture of different difunctional (meth)acrylate monomers in a special ratio or a mixture of special monofunctional and difunctional (meth)acrylate monomers.

However, due to the complex reaction behaviour of multi-component compositions, a lot of effort is needed to achieve sometimes only marginal improvements of volume shrinkage, if a sufficient level of mechanical properties is to be maintained.

U.S. Pat. No. 4,744,827 describes (meth)acrylic acid derivatives of tricyclodecanes and their use.

US 2004/0209990 refers to a low shrinking polymerizable dental material comprising a mixture of organic or inorganic filler and a polymerizable resin matrix having a volumetric polymerization shrinkage of less than 2 vol.-%.

WO 2005/107626 relates to dimer acid-derived dimethacrylates and their use in dental restorative compositions.

JP 2306955 is focussing 2,2-bis(4"-hydroxyphenyl) hexafluoropropane and/or its polyalkylene glycol esters. It is stated that these molecules can be useful as crosslinkers in coatings, adhesives, inks, electrical insulators, optical materials, photographical materials, printing, dental cements, fibers, photoresists, pharmaceutical products etc. However, it has been found that bisphenol A derivatives containing $CF_3$ moieties sometimes show a comparable low refractive index and are not always suitable in the dental field.

From the above it becomes clear that there is still room for improvement, especially with regard to the requirements to be fulfilled with respect to modern dental materials.

SUMMARY OF THE INVENTION

In one aspect the invention is directed to a dental composition comprising a monomer or a mixture of monomers which is represented by formula (1) below and mixtures containing such a monomer:

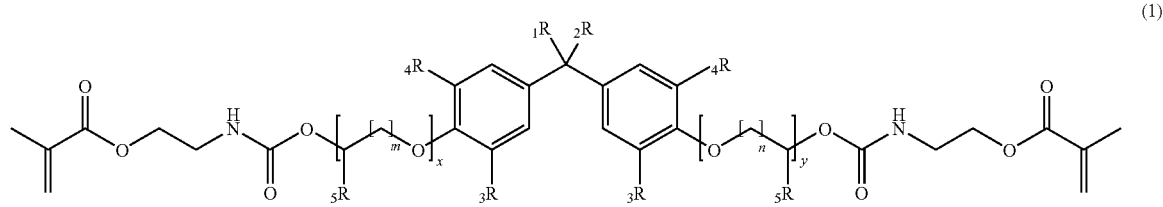

with
- $_{1,2}R$ independently selected from H, alkyl (such as C1 to C4, including $CH_3$ and $C_2H_5$), and Phenyl,
- $_{3,4}R$ independently selected from H and alkyl (such as C1 to C4, including $CH_3$ and $C_2H_5$), and halogen (including Cl, Br, F),
- $_5R$ independently selected from H, alkyl (such as C1 to C4, including $CH_3$ and $C_2H_5$)
- m, n=1, 2 and
- x+y=2 to 10 or 2 to 9 or 2 to 8, including 4, 6.5 and 8.5,
- in particular with the proviso that if m=n=2, than x+y=2 and if m=n=1, than x+y=4 to 10.

In another aspect the invention is directed to a process of producing such a monomer or a mixture of monomers comprising the step of reacting an isocyanato ethylmethacrylate with a dihydroxyl functional bis-phenol derivative.

In a further aspect the invention is directed to a process of using such a monomer or a mixture of monomers for the production of dental materials.

The invention is also directed to a dental composition comprising
- a) a resin matrix, the resin matrix comprising at least about 10 wt.-% of the whole composition and
- b) a filler matrix, the filler matrix comprising at least about 40 wt.-% of the whole composition,
- c) an initiator being able to start the hardening process of the hardenable components being present in the resin matrix,
- d) optionally further additives selected from the group consisting of pigments, colourants, stabilizers, retarders, plasticizers, flavorants, anti-microbials, fragrance, agents that impart fluorescence and/or opalescence and fluoride releasing materials and mixtures thereof, wherein the resin matrix comprises monomers or a mixture of monomers which can be summarized under the formula (1) given above.

In certain embodiments of the invention, the resin of the dental composition comprises at least about 10, 20, 30, 40 or 50 wt.-% of the inventive monomers.

Still further, the invention is directed to a method of using the dental composition as described in the text of the invention as or for the production of artificial crowns, anterior or posterior fillings, casting materials, cavity liners, cements, coating compositions, mill blanks, orthodontic devices, restoratives, prostheses or sealants.

Surprisingly it has been found that the monomer or the mixture of monomers characterized by formula (1) above show well balanced properties with respect to viscosity, refractive index, molecular weight and shrinkage value, especially if cured in the presence of other components.

A sufficient low viscosity may facilitate the handling procedure and the mixing of the monomer with other components of a composition.

A refractive index matching with the refractive index of other components such as fillers may help in providing a composition fulfilling the practitioner needs with respect to aesthetic properties. It has been found that monomers bearing certain halogen containing groups (e.g. $CF_3$) sometimes have a lower refractive index compared to monomers not containing such halogen containing groups.

A sufficient high molecular weight of the monomer may contribute to meet toxicological requirements which need to be fulfilled if the substance is to be used in the medical/dental field. A sufficient high molecular weight may also contribute to a reduced shrinkage of the monomer during or after the curing process.

In certain embodiments, the monomers or mixture of monomers used in the present invention show the following features:
- The monomers are methacrylate functional and have a molecular weight comparable to commercially available monomers (such as Bis-GMA, oxetanylated (2) bis-phenol A dimethacrylate, ethoxylated (4) bis-phenol A dimethacrylate, ethoxylated (6) bis-phenol A dimethacrylate, ethoxylated (10) bis-phenol A dimethacrylate, Tricyclo[$5.2.1.0^{2,6}$]decane dimethanole dimethacrylate, Tricyclo[$5.2.1.0^{2,6}$]decane dimethanole diacrylate).
- The monomers are difunctional with respect to the methacrylate group.
- The backbone of the monomers is based on alkoxylated bisphenols (including Bisphenol F, Bisphenol A, Bisphenol AP, each alkoxylated on the phenolic hydroxyl groups to form dihydroxyl functional bisphenol derived ethers like e.g. ethoxylated and/or propoxylated and/or oxetanylated bisphenol A).
- The methacrylate groups are attached via an urethane linkage onto the central backbone. Without wishing to be bound to a particular theory it is believed that this helps in improving properties in terms of high durability and/or reduced polymerization shrinkage.
- The monomers are obtainable using e.g. 2-isocyanatoethylmethacrylate (IEM; 2-methacroyloxyethylisocyanate, CAS no. 30674-80-7) as isocyanato functional building block, which can be reacted with dihydroxyl functional central backbones as building blocks.

Certain embodiments of the dental composition according to the invention comprising such a monomer or mixture of these monomers show improved mechanical properties. It has been found that this improvement in properties can sometimes be obtained without increasing the amount of inorganic filler (compared to commercially available composite materials).

Moreover, it has been found that with respect to certain embodiments of the inventive composition there is also neither a need to add pre-polymeric compounds having a high molecular weight (Mw above about 1500) nor to use a certain mixture of specific monomers in a specific ratio in order to reduce the polymerization shrinkage and/or to maintain or even improve the durability compared to commercially available materials.

Thus, certain embodiments of the inventive dental composition show a unique combination of features including reduced polymerization shrinkage combined with improved durability.

To a certain extend these features of the dental composition are influenced by using the inventive monomers or mixture of monomers having a comparable high molecular weight (e.g. above about 600) combined with an acceptable viscosity (e.g. below about 500 Pa*s at 23° C.) and an acceptable refractive index being in the range of e.g. 1.51 to 1.54 (nD).

To determine whether a certain composition is useful or not, mechanical properties like compressive strength (CS), flexural strength (FS), and E-modulus of the cured composition are typically measured. Besides these, the wear resistance of the cured composite (e.g. measured as a Two Body Wear Resistance according to ACTA) can be of importance, as well as the durability (i.e. the long term performance) of the cured composition under relevant conditions (e.g. at body temperature in water).

To predict a sufficient durability of the cured composite in a patient's mouth over a certain period of time various tests are suggested. E.g. a sufficient level of initial mechanical properties of the cured composite in combination with only a smooth reduction of this level of initial mechanical properties over a certain period of time under relevant conditions is sometimes considered to be a useful concept.

This evaluation can be done e.g. by storing the cured composition at body temperature (37° C.) in water for a definite period of time with accompanying measurements. But also stress tests like accelerated aging studies (e.g., heating the cured composition in water for 10 h to a temperature of about 93° C.) might be a useful concept to get a faster prognosis of the potential durability of the cured composite, especially if the initial data is compared with the data measured after stress. A more detailed description of these measurements can be found in the example section.

Definitions

A "dental composition" within the meaning of the invention is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices.

A "monomer" within the meaning of the invention is any chemical substance which can be characterized by a chemical formula, bearing polymerizable groups (including (meth) acrylate groups) which can be polymerized to oligomers or polymers thereby increasing the molecular weight. The molecular weight of monomers can usually simply be calculated based on the chemical formula given.

A "hardenable compound" within the meaning of the invention is any compound which can be cured or solidified e.g. by heating to cause polymerization, chemical crosslinking, radiation-induced polymerization or crosslinking or using a redox initiator. A hardenable compound may contain only one, two, three or more polymerizable groups. A typical example of a polymerizable group is a unsaturated carbon group, such as a vinyl group being present i.a. in a (methyl) acrylate group.

The "resin matrix" within the meaning of the invention contains all hardenable compounds (monomers, oligomers and/or polymers) being present in the hardenable composition. The resin matrix may contain only one hardenable compound or a mixture of different hardenable compounds. The inventive monomer or mixture of monomers is comprises in the resin matrix as well.

The "filler matrix" within the meaning of the invention contains all fillers being present in the hardenable composition. The filler matrix may contain only one filler or a mixture of different fillers.

"Dispersed within the resin" means that filler particles are present in the resin as discrete, unassociated (i.e. non-agglomerated and non-aggregated) particles.

A "nano-sized filler" within the meaning of the invention is a filler, the individual particles thereof have a size in the region of nanometers, e.g. an average particle diameter of less than about 200 nm. Useful examples are given in U.S. Pat. Nos. 6,899,948 and 6,572,693, the content of which especially with regard to nano-sized silica particles is herein incorporated by reference.

An "initiator or initiator system" within the meaning of the invention is a substance being able to start the curing process of a hardenable compound.

A "curing, hardening or setting reaction" within the meaning of the invention is used interchangeable and refers to a reaction wherein physical properties such as viscosity and hardness of a composition changes over the time due to a chemical reaction between the individual components.

A "derivative" within the meaning of the invention is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

The invention relates to a dental composition comprising a hardenable monomer or mixture of monomers according to formula (1) above. In the text of the invention, these monomers are also referred to as monomer(s) (A1). Other hardenable monomers which might be present in the hardenable composition are referred to as hardenable components (A2). These hardenable components (A2) can be used together with the inventive monomer(s) (A1).

In a specific embodiment the monomer or mixture of inventive monomers fulfils at least one of the following parameters:

Refractive index: from about 1.51 or about 1.52 or about 1.53 to about 1.54 (nD), Molecular weight: above about 600 or in a range of about 600 to about 1000, and/or Viscosity: below about 500 Pa*s at 23° C. or in a range of about 10 to about 500 Pa*s at 23° C.

An example of a preferred embodiment of the inventive monomer or mixture of monomers is given by the formula (2) below:

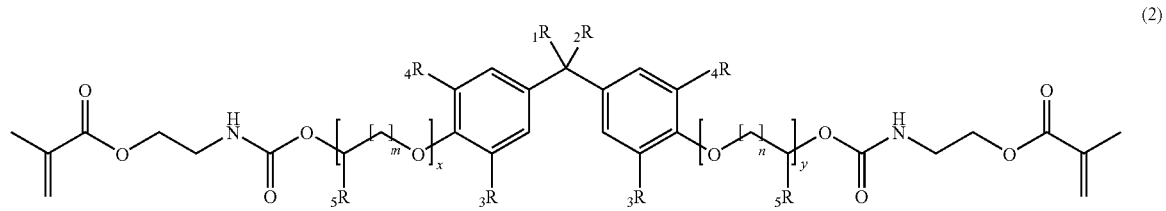
(2)

with
$_{1,2}R$ independently selected from H, CH$_3$, and Phenyl,
$_{3,4}R$ independently selected from H and CH$_3$, Br and Cl,
$_5R$ independently selected from H and CH$_3$,
m, n=1, 2 and
x+y=2 to 10 or 2 to 9 or 2 to 8, including 4, 6.5 and 8.5.

Another example of another preferred embodiment of the inventive monomer or mixture of monomers is given by formula (3) below:

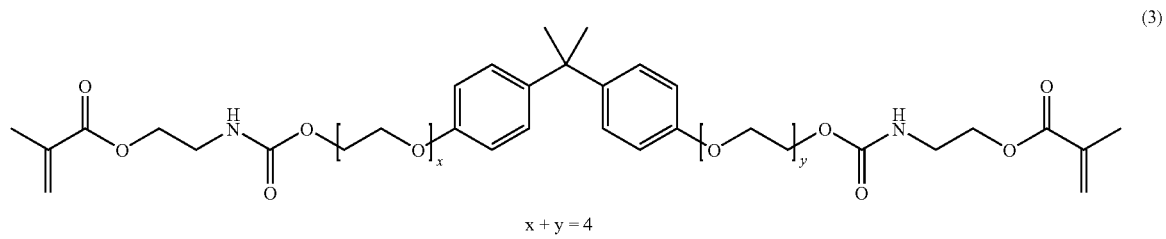
(3)

x + y = 4

Examples of other monomers or mixtures of monomers which can be used in the present invention include:

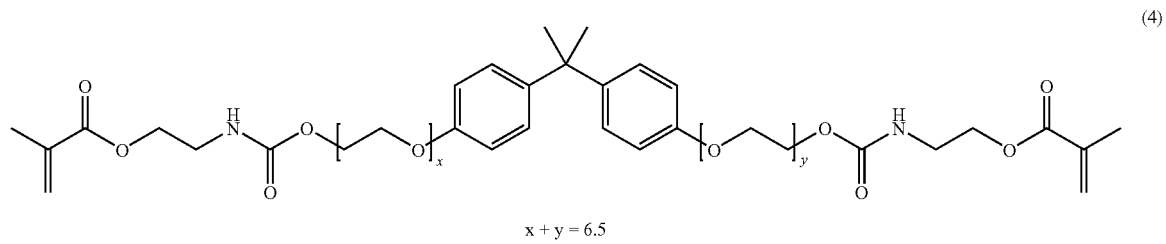
(4)

x + y = 6.5

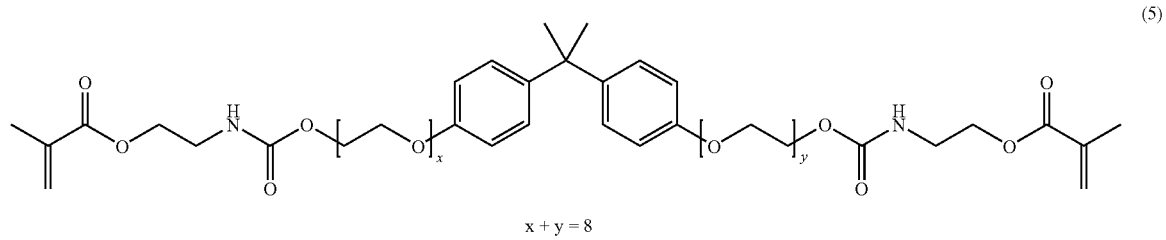
(5)

x + y = 8

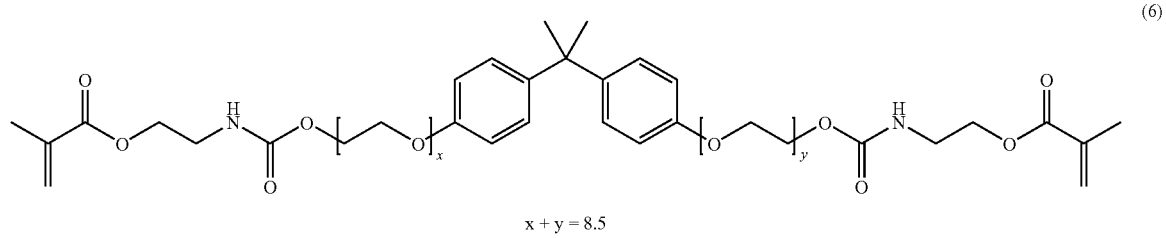
(6)

x + y = 8.5

-continued

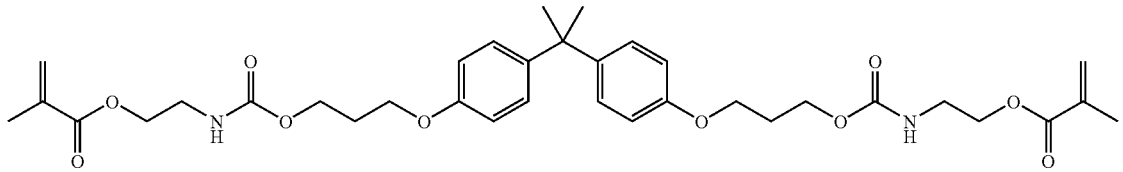

(7)

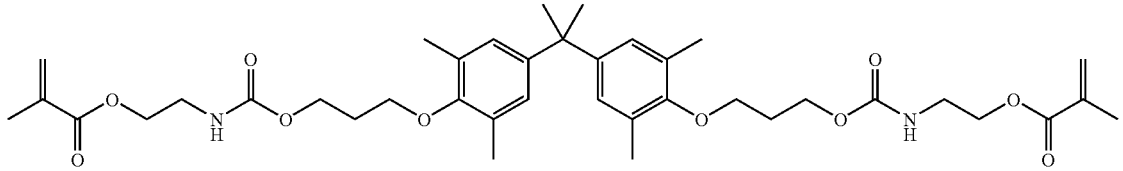

(8)

The monomer or mixture of monomers represented by either of the formulas (1) to (8) is obtainable or can be produced according to a quite simple process, preferably in a one step one pot addition reaction, if the right reaction components are chosen.

According to one embodiment the process comprises the step of reacting isocyanato ethylmethacrylate (IEM) with a dihydroxyl functional bis-phenol derivative (such as Seppic Dianol 220 (CAS no. 901-44-0), Seppic Dianol 240 (CAS no. 32492-61-8), Seppic Dianol 265 (CAS no. 32492-61-8), Seppic Dianol 285 (CAS no. 32492-61-8), Seppic Simulsol BPJE (CAS no. 32492-61-8), Seppic Simulsol BPJE/AP (CAS no. 32492-61-8), Seppic Dianol 320 (CAS no. 37353-75-6), Seppic Dianol 340, Seppic Simulsol BPPE, Seppic Simulsol BPPE/A, Cognis PHOTONOL PHO-7028 (CAS no. 32492-61-8), Sigma-Aldrich Bisphenol A Ethoxylate (EO/Phenol 2 (CAS no. 32492-61-8), EO/Phenol 3 (CAS no. 32492-61-8)), Sigma-Aldrich Bisphenol A Propoxylate (PO/Phenol 1, CAS no. 37353-75-6), Monomer-Polymer & Dajac Labs Ethoxylated Bisphenol A (CAS no. 32492-61-8).

A catalyst in an appropriate amount (e.g. 500 ppm) such as dibutyl tindilaurate (DBTDL) or bismuth neodecanoate (e.g. Shepherd Bicat 8108M, ABCR Bismuth (III) neodecanoate, superconductor grade, about 60% in neodecanoic acid (15-20% Bi), or Strem Chemicals Bismuth (III) neodecanoate, superconductor grade, about 60% in neodecanoic acid (15-20% Bi) can be used, but is not mandatory.

The reaction can typically be carried out in a temperature range of about 40 to about 70° C., preferably under dry conditions (e.g. dry air). The reaction can be carried out in common solvents (including cyclohexane, toluene, ethylacetate, diethylether, methyl-tert-butyl-ether, tetrahydrofurane) or without a solvent.

To prevent unwanted radical polymerization during the synthesis, a stabilizer in an appropriate amount (e.g. 50 to 500 ppm) such as 3,5-di-tert.-butyl-4-hydroxy-toluene (BHT), 4-methoxyphenol (MOP), or hydroquinone (HQ) can be used, but is not mandatory.

Completion of the reaction can be determined by IR spectroscopy, especially focussing on the NCO band showing an absorption at about 2273 cm$^{-1}$.

A typical process can be summarized as follows:

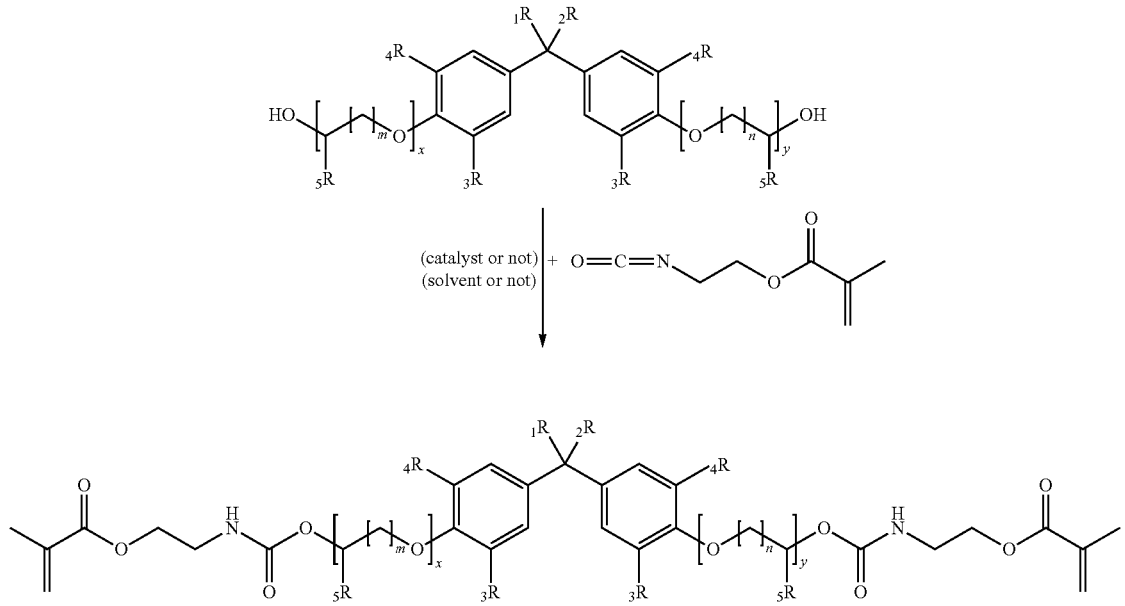

wherein the indices have the meaning as defined above for formula (1).

The monomer or mixtures or monomers can be used for producing dental compositions. In a preferred embodiment the monomers or mixture of monomers can be used directly out of the reaction vessel without further purification steps.

The invention also relates to a dental composition comprising this monomer or mixture of monomers without a filler matrix.

In certain embodiments the inventive composition without a filler matrix fulfils at least one of the following parameters after hardening:
- Flexural Strength (MPa): at least about 90 or at least about 100 or at least about 110 determined according to ISO 4049,
- E-Modulus (GPa): at least about 1.9 or at least about 2.1 or at least about 2.3 determined according to ISO 4049, and/or
- Volume Contraction (vol.-%): less or equal than about 5.5 or less or equal than about 5.3 or less or equal than about 5.1 using a Helium Pyconmeter Micrometritics Accu-Pyc 1330.

The invention also relates to a dental composition comprising the inventive monomer or mixture of monomers together with a filler matrix.

In certain embodiments the inventive composition containing a filler matrix fulfils at least one of the following parameters after hardening:
- compressive strength (MPa): at least about 320 or at least about 340 or at least about 350, determined according to ISO 9917 using cubic specimen (dimensions 3 mm×3 mm×5 mm),
- flexural strength (MPa): at least about 120 or at least about 130 or at least about 140 determined according to ISO 4049,
- E-modulus (GPa): at least about 9 or at least about 10 or at least about 11 determined according to ISO 4049, and/or
- bonded disk shrinkage-strain (vol.-%): less or equal than about 1.6 or less or equal than about 1.5 or less or equal than about 1.4 determined according to the Watts protocol.

For certain embodiments (e.g. dental composite materials), a combination of the following parameters can be preferred: compressive strength (e.g. at least about 350 MPa) and flexural strength (e.g. at least about 140 MPa). For these embodiments a bonded disk shrinkage-strain (Watts protocol) below about 1.50 vol.-% can be preferred.

The inventive dental composition comprises a resin matrix. The resin matrix comprises at least about 10 wt.-% or at least about 15 wt.-% or at least about 16 wt.-% of the whole composition. The resin matrix can be comprised of one hardenable component or a mixture of different hardenable components.

At least about 10, 20, 30, 40, 50 or 60 wt.-% of the resin matrix can be comprised of component(s) which can be summarized under the formula (1) above.

According to the invention, the resin matrix can be comprised of
- the inventive monomer (A1) or mixtures thereof as hardenable compound alone,
- a mixture of the inventive monomers (A1) or mixtures thereof together with another hardenable component (A2) being different from the monomer (A1) or,
- a mixture of inventive monomers (A1) or mixtures thereof together with mixtures of other hardenable components (A2) being different from the monomer (A1).

That is, the resin matrix can be comprised of 1, 2, 3 or 4 hardenable components only, at least one of which can be summarized under the formula (1) above.

In a further embodiment of the invention, the resin matrix does not contain more than about 4 or more than about 3 different hardenable components with one or two polymerizable groups.

In another embodiment of the invention, the resin matrix only contains hardenable components having two polymerizable groups, but no hardenable components with only one polymerizable group.

In yet a further embodiment, the other or further hardenable component(s) (A2), which might be present in the resin matrix in combination with the inventive monomer or monomer mixture, include monomers, oligomers, and polymers having one or more polymerizable (e.g. ethylenically unsaturated) groups.

In the class of hardenable resins having free radically active functional groups, suitable materials for use in the invention contain at least one ethylenically unsaturated bond, and are capable of undergoing an addition polymerization. Such free radically polymerizable materials include mono-, di- or polyacrylates and methacrylates such as methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

Preferred ethylenically unsaturated monomers are methacrylate and acrylate monomers, such as methyl (meth)acrylate, n- or i-propyl (meth)acrylate, n-, i- or tert-butyl (meth)acrylate and 2-hydroxy(meth)acrylate, 2-(meth)acryloxytetrahydrofuran, 2-(((alkylamino)carbonyl)oxy)ethyl (meth)acrylates, di(meth)acrylates of propanediol, butanediol, hexanediol, octanediol, nonanediol, decanediol and eicosanediol, tetrahydrofurfuryl (meth)acrylate, di(meth)acrylates of ethylene glycol, of polyethylene glycols and of polypropylene glycols, di(meth)acrylates of ethoxylated bis-phenol A, for example 2, 2'-bis(4-(meth)acryloxytetraethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8(9)-tricyclo[5.2.1.0$^{2,6}$]decylmethyl triglycolate. Suitable are also 2,2-bis-4-(3-methacryloxy-2-hydroxypropoxy)phenylpropane (Bis-GMA), 2,2-bis-4-(3-methacryloxypropoxy)phenylpropane, triethylene glycol dimethacrylate (TEGDMA), 7,7,9-trimethyl-4,13-dioxo-3,14-dioxa-5,12-diazahexadecane-1,16-dioxy dimethacrylate (UDMA), urethane (meth) acrylates and di(meth)acrylates of bishydroxymethyltricyclo-(5.2.1.0$^{2,6}$)decane.

These ethylenically unsaturated monomers can be employed in the inventive dental compositions either alone or in combination with further ethylenically unsaturated monomers.

Other hardenable components which can be added include urethane methacrylates including low-molecular-weight compounds, such as 7,7,9-trimethyl-4,13-dioxo-3,14-dioxa-5,12-diazahexadecane-1,16-dioxy dimethacrylate and/or oligomeric or polymeric compounds, such as polyester urethane (meth)acrylates, polyether urethane (meth)acrylates, polycarbonate urethane (meth)acrylates and poly(meth)acrylate urethane (meth)acrylates. The molecular weight of these compounds is preferably less than 20,000 g/mol, particularly less than 15,000 g/mol and in particular less than 10,000 g/mol.

The hardenable component (A2) can be present in an amount of at least about 5 wt.-% or at least about 10 wt.-% or at least about 15 wt.-% with respect to the whole composition.

The hardenable component (A2) can be present in an amount up to about 40 wt.-% or up to about 35 wt.-% or up to about 30 wt.-% with respect to the whole composition.

The inventive dental composition comprises a filler matrix. The filler matrix can be comprised of one filler or a mixture of different fillers.

The nature of filler of the inventive composition is not particularly limited. The size of the filler particles should be such that a homogeneous mixture with the hardenable component(s) forming the resin matrix can be obtained.

Useful fillers include fumed silica, fillers based on fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate.

The silica is usually dispersed within the resin matrix. The silica particles used in the dental compositions of the invention preferably have an average diameter of less than about 200 nm; more preferably, the particles are less than about 100 nm in average diameter. These measurements are preferably based on a TEM (transmission electron microscopy) method, whereby a population is analyzed to obtain an average particle diameter. A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The average surface area of the silica particles is preferably greater than about 15 m$^2$/g more preferably greater than about 30 m$^2$/g.

Once dispersed in the resin, the silica particles are in a discrete (individual) and unassociated (i.e. non-agglomerated, non-aggregated) condition. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The silica particles which can be used in the dental materials of the invention are preferably substantially spherical and substantially non-porous. Although the silica is preferably essentially pure, it may contain small amounts of stabilizing ion such as ammonium and alkaline metal ions.

Suitable fumed silicas include for example, products sold under the tradename AEROSIL series OX-50, -130, -150, and -200 available from Degussa AG, (Hanau, Germany), and CAB-O-SIL M5 available from Cabot Corp (Tuscola, Ill.).

Useful fluoroaluminosilicate glasses include silanol treated fluoroaluminosilicate glass fillers, as described in U.S. Pat. No. 5,332,429, the disclosure of which is expressly incorporated by reference herein. For example, a fluoride releasing glass may be added to the dental composition to provide the benefit of long-term release of fluoride in use, for example in the oral cavity.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 can be preferred. The heavy metal oxide should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

In a preferred embodiment the filler matrix comprises a nano-sized filler including nano-sized silica.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329. In a preferred embodiment where the hardenable resin employs a cationic initiation system, the starting silica is preferably acidic (such as Nalco 1042).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental composition of the invention.

The nature and amount of filler(s) which can be used may not only have an effect on the viscosity of the composition but also may influence the aesthetic appearance (such as high gloss, high polish retention) and mechanical properties including hardness.

The filler matrix can comprise at least about 25 wt.-% or at least about 30 wt.-% or at least about 40 wt.-% or at least about 50 wt.-% of the whole composition.

The filler matrix can comprise up to about 90 wt.-% or up to about 85 wt.-% or up to about 80 wt.-% of the whole composition.

The amount of filler to be used in the filler matrix usually depends on the purpose for which the dental composition should be used.

Temporary crown and bridge materials usually do not contain a high amount of fillers. With respect to these compositions, the filler content usually is in a range of about 30 to about 60 wt.-% with respect to the whole composition.

In dental filling materials, which typically contain a higher amount of fillers compared to temporary crown and bridge materials, the filler content is usually in a range of about 60 to about 85 wt.-% with respect to the whole composition.

The inventive dental composition also comprises an initiator or initiator system being able to start the curing process of the hardenable components being present in the resin matrix.

Dental materials of the invention can be chemically curable, heat curable or light curable compositions. Light curable materials should have an appropriate initiator system. Chemically curable materials can be auto-cured (e.g. via redox initiators). Alternatively, the materials of the invention can be hardened by a combination of auto- and light-cure.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between about 200 and about 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat. No. 4,071,424, which is herein incorporated by reference. Alternatively, the resin can be combined with a three componentsor ternary photoinitiator system such as described in U.S. Pat. No. 5,545,676 which is incorporated herein by reference.

In the ternary photoinitator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: $ACO(X)_b B$, where X is CO or $CR^5R^6$, where $R^5$ and $R^6$ can be the same or different, and can be hydrogen, alkyl, alkaryl or aralkyl, b is zero or one, and A and B different and can be substituted (having one or more non-interfering substituents) can be the same or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Alternatively, free-radical initiators useful in the invention include the class of acylphosphine oxides, as described in U.S. Pat. No. 4,737,593. Such acylphosphine oxides are of the general formula

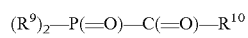

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethyl-amino) benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye counterion complex initiators comprising a borate anion and a complementary cationic dye.

Borate salt photoinitiators are described, for example, in U.S. Pat. Nos. 4,772,530, 4,954,414, 4,874,450, 5,055,372, and 5,057,393, the disclosures of which are incorporated herein by reference.

Borate anions useful in these photoinitiators generally can be of the formula $R^1R^2R^3R^4B^-$, wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 15° C. under normal conditions or at elevated pressure. This procedure is preferred for initiating polymerization of materials occurring outside of the oral environment.

Organic peroxide compounds together with so-called activators are also suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451). Preferred malonyl sulfamides are 2,6-dimethyl-4-isobutyl-malonyl sulfamide, 2,6-diisobutyl-4-propylmalonyl sulfamide, 2,6-dibutyl4-propylmalonyl sulfamide, 2,6-dimethyl-4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. The heavy metal is suitably used in the form of soluble organic compounds. Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

If the inventive dental compositions contain a redox initiator system comprising organic peroxide and activator, peroxide and activator are preferably present in parts physically separated from one another and are homogeneously mixed together only immediately before use. If organic peroxide, copper compound, halide and malonyl sulfamide and/or barbituric acid are present next to each other, it is particularly useful for the organic peroxide, malonyl sulfamide and/or barbituric acid and the combination of copper compound/halide to be present in three constituents physically separated from one another. For example, the combination of copper compound/halide, polymerizable monomers and fillers can be kneaded to a paste and the other components kneaded to two separate pastes each with a small quantity of fillers or in particular thixotropic auxiliaries, such as silanized silicic acid, and a plasticizer, for example phthalate. On the other hand, the polymerizable monomers can also be present together with organic peroxide and fillers. Alternatively, a distribution of organic peroxide, copper compound, halide and malonyl sulfamide and/or barbituric acid can be realized according to U.S. Pat. No. 6,852,775 (corresponding to DE 199 28 238).

The initiator or initiator system is typically provided in the dental composition of the invention in an amount effective to initiate or enhance the rate of cure or hardening of the resin system.

The initiator can be present in an amount of at least about 0.1 wt.-% or at least about 0.2 wt.-% or at least about 0.3 wt.-% with respect to the whole composition. The initiator can be present in an amount up to about 3 wt.-% or up to about 2 wt.-% or up to about 1.8 wt.-% with respect to the whole composition containing a filler matrix.

The inventive composition can optionally contain further additives.

Typical additives include pigments and colorants. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethyl-amino) methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive functionality so that they will be copolymerized with the resin.

Additives, which can be added, also include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence and fluoride releasing materials.

In order to increase the flexibility of the dental material, it is also possible to add soluble organic polymers including polyvinyl acetate, and copolymers thereof.

There is no absolute need for these additives to be present, so additives might not be present at all. However, if they are present they are typically present in an amount of at least about 0.01 wt.-% or at least about 0.5 wt.-% or at least about 1 wt.-% with respect to the whole composition.

The additives can be present in an amount up to about 25 wt.-% or up to about 20 wt.-% or up to about 15 wt.-% with respect to the whole composition.

In a further embodiment, the inventive dental composition comprises
- the filler matrix in an amount of about 35 to about 90 wt.-% or about 40 to about 85 wt.-% or about 45 to about 82 wt.-%,
- the resin matrix in an amount of about 10 to about 65 wt.-% or about 15 to about 60 wt.-% or about 18 to about 50 wt.-%,
- the initiator in an amount of about 0.1 to about 3 wt.-% or about 0.2 to about 2 wt.-% or about 0.3 to about 1.8 wt.-%,
- optionally additives in an amount of about 0 to about 25 wt.-% or about 0.1 to about 15 wt.-% or about 0.2 to about 5 wt.-%, wt.-% with respect to the whole composition.

In a specific embodiment of the invention, the composition does not necessarily contain polymerizable di- or poly(meth)acrylates obtainable e.g. by reaction of with diisocyanates with diols) which are used i.a. in WO 01/95862 in order to reduce the polymerisation shrinkage.

Certain embodiments of the invention are essentially free from low boiling solvents (e.g. boiling point below about 150° C. at ambient pressure). In this context "essentially free from" means that the content is typically below about 1 wt.-% or below about 0.5 wt.-% or below about 0.1 wt.-% with respect to the whole composition.

In another embodiment, the monomers or hardenable compounds comprised in the resin matrix of the inventive composition do not have voluminous or bulky residues (such as straight-chain or branched $C_4$ to $C_{25}$ alkyl groups), which are used i.a. in WO 05/107626 in order to reduce the polymerisation shrinkage.

The dental compositions of the invention can be used for example, as artificial crowns, anterior or posterior fillings, casting materials, cavity liners, cements, coating compositions, mill blanks, orthodontic devices, restoratives, prostheses and sealants.

In a preferred aspect, the dental material is a dental filling material. The dental filling materials of the invention can be placed directly in the mouth and cured (hardened) in situ, or alternatively, may be fabricated into a prosthesis outside the mouth and subsequently adhered in place inside the mouth.

The invention is also directed to the use of the inventive monomers or mixture of monomers for the production of a dental composition, the process of using comprising the steps of:
a) placing the dental composition comprising the monomer or mixture of monomers according to formula (1) in contact with a tooth,
b) hardening the composition.

The inventive dental composition is typically stored in a container until use. Depending on the initiator system chosen, various containers can be suitable.

If the dental composition is provided as a one-component system, it can be stored in a container having only one chamber such as a compule. The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. Nos. 5,893,714 and 5,865,803, the content of which with regard to the description of compules or containers is herewith incorporated by reference.

Alternatively, if the dental composition is provided as a two-component system, it can be stored in a dual-chamber container or cartridge and is mixed before use.

Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland).

The invention is hereinafter described by examples. The examples are given for illustrative purpose only and are not intended to limit the scope of the invention.

EXAMPLES

If not otherwise indicated, all percentages are given in weight percentages and all processes are carried out under ambient conditions.

TABLE 1

Abbreviations

| Abbreviation | Description | Source | Component |
|---|---|---|---|
| P-IEM | 2,2-Bis{4-[3-(N-2-methacroyloxyethyl)-carbamoyloxypropyloxy]-phenyl}propane, reaction product of oxetanylated (2) bis-phenol A (P-Alcohol) and IEM | Ex. 1 | a) |

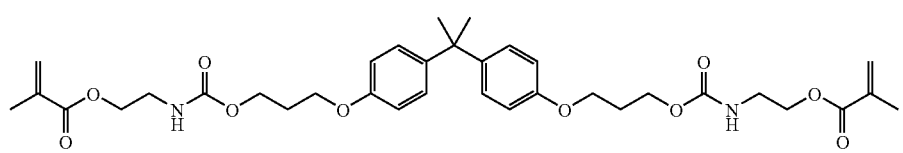 [SMILES: C=C(C)C(=O)OCCNC(=O)OCCCOc1ccc(C(C)(C)c2ccc(OCCCOC(=O)NCCOC(=O)C(=C)C)cc2)cc1]

M = 654.8
nD = 1.5356
η = 460 Pa * s

TABLE 1-continued

Abbreviations

| Abbreviation | Description | Source | Component |
|---|---|---|---|
| D-IEM | 2,2-Bis{4-(2-[2-(N-2-methacroyloxyethyl)-carbamoyloxyethyloxy]-ethyloxy)-phenyl}propane, reaction product of ethoxylated (4) bis-phenol A and IEM<br><br>x + y = 4<br><br>M = 714.8<br>nD = 1.5323<br>η = 165 Pa * s | Ex. 2, 6, 10, 11 | b) |
| D2-IEM | reaction product of ethoxylated (6.5) bis-phenol A and IEM<br><br>x + y = 6.5<br><br>M = 820.3<br>nD = 1.5257<br>η = 36 Pa * s | Ex. 7 | c) |
| D3-IEM | reaction product of ethoxylated (8.5) bis-phenol A and IEM<br><br>x + y = 8.5<br><br>M = 907.1<br>nD = 1.5197<br>η = 15 Pa * s | Ex. 8, 10 | d) |
| T-IEM | TCD-Alcohol - IEM, reaction product of tricyclo[5.2.1.02,6]decane dimethanole (TCD-Alcohol DM) and IEM<br><br>M = 505<br>nD = 1.5099<br>η = 390 Pa * s | Comparative Ex. 2 | e) |
| CPQ | Camphorquinone (CAS no. 10373-78-1) | | f) |
| EDMAB | 4-Dimethylamino benzoic acid ethyl ester (CAS no. 10287-53-3) | | g) |
| DPIPF6 | Diphenyliodonium hexafluorophosphate (CAS no. 58109-40-3) | | h) |

TABLE 1-continued

| Abbreviation | Description | Source | Component |
|---|---|---|---|
| TMP-IEM | 2,2-Bis{3,5-dimethyl-4-[3-(N-2-methacroyloxyethyl)-carbamoyloxypropyloxy]-phenyl}propane, reaction product of oxetanylated (2) tetramethyl bis-phenol A (TMP-Alcohol) and IEM | Ex. 3 | i) |

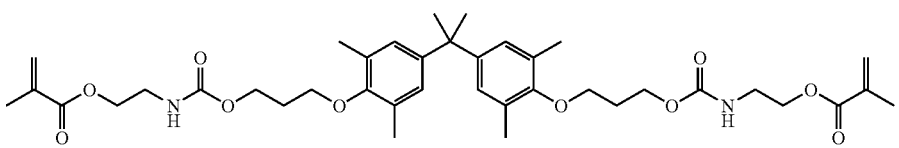 [SMILES: C=C(C)C(=O)OCCNC(=O)OCCCOc1c(C)cc(C(C)(C)c2cc(C)c(OCCCOC(=O)NCCOC(=O)C(=C)C)c(C)c2)cc1C]

M = 792.8
nD = 1.5302
η = >750 Pa * s

| TCP-IEM | 2,2-Bis{3,5-dichloro-4-[3-(N-2-methacroyloxyethyl)-carbamoyloxy-propyloxy]-phenyl}propane, reaction product of oxetanylated (2) tetrachloro bis-phenol A (TCP-Alcohol) and IEM | Ex. 4 | j) |

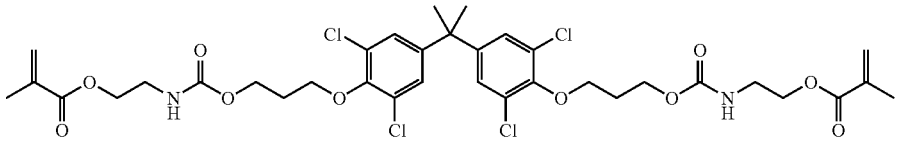 [SMILES: C=C(C)C(=O)OCCNC(=O)OCCCOc1c(Cl)cc(C(C)(C)c2cc(Cl)c(OCCCOC(=O)NCCOC(=O)C(=C)C)c(Cl)c2)cc1Cl]

M = 710.9
nD = 1.5391
η = 400 Pa * s

| HFP-IEM | 1,1,1,3,3,3-Hexafluoro-2,2-bis{4-[3-(N-2-methacroyloxyethyl)-carbamoyloxypropyloxy]-phenyl}propane, reaction product of oxetanylated (2) hexafluoro bis-phenol A (HFP-Alcohol) and IEM | Comparative Ex. 3 | k) |

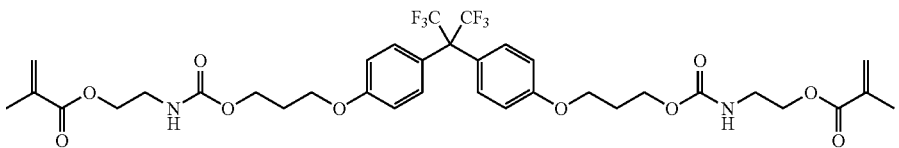 [SMILES: C=C(C)C(=O)OCCNC(=O)OCCCOc1ccc(C(c2ccc(OCCCOC(=O)NCCOC(=O)C(=C)C)cc2)(C(F)(F)F)C(F)(F)F)cc1]

M = 762.7
nD = 1.5095
η = >750 Pa * s

| D5-IEM | reaction product of propoxylated (4) bis-phenol A and IEM | Ex. 9 | l) |

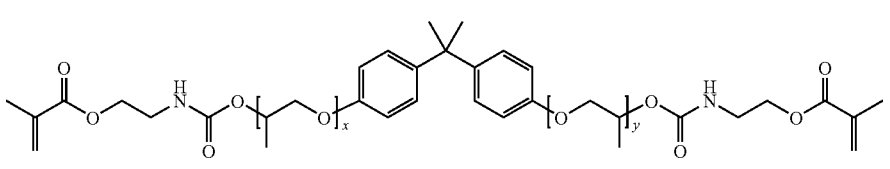

x + y = 4

M = 752
nD = 1.5214
η = 750 Pa * s

TABLE 1-continued

Abbreviations

| Abbreviation | Description | Source | Component |
|---|---|---|---|
| BUM | Bis-GMA diurethane dimethacrylate, η = 1060 Pa * s, reaction product of Bis-GMA and IEM | Comparative Ex. 1 | m) |

M = 822.9
nD = 1.5267
η = 1060 Pa * s

| Bis-GMA | | Comparative Ex. 4 | n) |
|---|---|---|---|

(CAS no. 1565-94-2)

M = 512.6
nD = 1.551
η = 690 Pa * s
Oxetanylated (2) Bis-Phenol A Dimethacrylate

| | | Comparative Ex. 5 | o) |
|---|---|---|---|

M = 480
nD = 1.5375
η = 1 Pa * s
Tricyclo[5.2.1.0$^{2,6}$]decane Dimethanole Diacrylate

| | | Comparative Ex. 6 | p) |
|---|---|---|---|

(CAS no. 42594-17-2)

M = 304.4
nD = 1.505
η = 0.3 Pa * s

TABLE 1-continued

Abbreviations

| Abbreviation | Description | Source | Component |
|---|---|---|---|
| TEGDMA | Triethyleneglycol dimethacrylate (CAS no. 109-16-0) M = 286.33 nD = 1.4621 $\eta$ = 0.03 Pa * s | Comparative Ex. 7, | q) |
| | Ethoxylated (4) Bis-Phenol A Dimethacrylate<br><br>x + y = 4<br>(CAS no. 41637-38-1)<br><br>M = 540.7<br>nD = 1.5330<br>$\eta$ = 0.6 Pa * s | Comparative Ex 8 | r) |
| Filler | Spray dried zirconia silica filler, <1 μm, surface treated | | s) |
| IEM | 2-Methacroyloxyethylisocyanate (CAS no. 30674-80-7) | | |
| BHT | 3,5-Di-tert.-butyl-4-hydroxy-toluene (CAS no. 128-37-0) | | |
| DBTDL | Dibutyltindilaurate (CAS no. 77-58-7) | | |
| bismuth neodecanoate | Bismuth (III) neodecanoate, superconductor grade, ~60% in neodecanoic acid (CAS no. 26896-20-8), 15-20% Bi (CAS no. 34364-26-6) | | |
| TCD-Alcohol DM | Tricyclo[5.2.1.0$^{2,6}$]decane dimethanole (CAS no. 26160-83-8) | | |
| P-Alcohol | 2,2-Bis[4-(3-hydroxypropyloxy)-phenyl]propane | | |
| TMP-Alcohol | 2,2-Bis[3,5-dimethyl-4-(3-hydroxypropyloxy)-phenyl]propane | | |
| TCP-Alcohol | 2,2-Bis[3,5-dichloro-4-(3-hydroxypropyloxy)-phenyl]propane | | |
| HFP-Alcohol | 1,1,1,3,3,3-Hexafluoro-2,2-bis[4-(3-hydroxypropyloxy)-phenyl]propane | | |

Measurements

Compressive Strength (CS)

For the measurement of compressive strength, 6 specimens of each material were prepared and the measurements were carried out according to ISO 9917 using a universal testing machine (Zwick Z 010), with the proviso that test specimens having the dimension of 3 mm×3 mm×5 mm were used in combination with a crosshead speed 4 mm/min. The compressive strength is given in MPa.

Flexural Strength (I)

The measurement of the flexural strength was carried out according to ISO 4049 using a universal testing machine (Zwick Z 010, crosshead speed 1 mm/min). The flexural strength is given in MPa.

Flexural Strength (II)

The FS (II) is given in MPa and was determined according to ISO 4049 but after additional stress test in water for 10 hours at 93° C.

E-Modulus (I)

The E-M (I) is given in GPa and was determined according to ISO 4049.

E-Modulus (II)

The E-M (II) is given in GPa and was determined according to ISO 4049 but after additional stress test in water for 10 hours at 93° C.

Two Body Wear Resistance (TBWR)

The Two Body Wear Resistance was determined according to ACTA relative to 3M ESPE's commercially available filling material Filtek™ Z250 (shade A3) chosen as reference value 1.00). A more detailed description is given in Pallav P., Occlusal Wear in Dentistry—Fundamental Mechanism, Clinical Implications, and Laboratory Assessment, Thesis Publishers, Amsterdam, 1996, p. 63-76.

Bonded Disk Shrinkage-Strain (SHR)

The Bonded Disk Shrinkage-Strain is given in % and was determined according to the Watts protocol as described in more detail in Dent. Mater. 1991, 7, 281-287.

Volume Contraction (VC)

The Volume Contration is given in % and was determined using a Helium Pycnometer Micromeritics AccuPyc 1330 and the corresponding method. A more detailed description is given in Dent. Mater. 1999, 15, 447-449.

Refractive Index ($n_D^{20}$)

The refractive index was measured with a Kruess AR 4 D device (refractometer according to Abbe's measure principle). The refractive index was measured at 20.0° C. at a wavelength of 589 nm.

Viscosity ($\eta$)

The viscosity was measured with a Haake RotoVisco RV1 device (rotor C60/1 for viscosities up to 8000 mPas or rotor C20/1 for viscosities above 8000 mPas together with stator P61). The viscosity was measured at 23.0° C. between two plane and parallel plates (i.e. stator and rotor). After activation and rectification of the system, the appropriate rotor was installed. Then the rotor was lowered and the distance between stator and rotor was adjusted to 0.052 mm (using Software RheoWin Pro Job Manager Software Version 2.94) for the viscosity measurement. Then the rotor was lifted and the material to be measured was given onto the stator (1.0 ml with rotor C60/1 or 0.04 ml with rotor C20/1). Without undue delay, the rotor was lowered into the preliminary adjusted measuring position. The material to be measured was tempered at 23.0° C. The shear rate for the measurement has to be adjusted to a value that the torque was at least 5000 μNm (therefore normally shear rates of 100, 200, 500, or 1000 s$^{-1}$ are used depending on the viscosity of the material to be measured). The measurement was started and run for 60 s. The viscosity values (Pas) were recorded starting 20 s after the start of measurement and the mean value of the recorded values was given as viscosity.

General Procedure A:

At a temperature of 50-55° C. IEM is added with mechanical stirring under an atmosphere of dry air to the dihydroxyl functional central backbone containing the used catalyst in the appropriate amount (if a catalyst is used at all) and 200 ppm of BHT (with respect to the total amount of the educts). Stirring is then continued at a temperature of 50° C. until there is no residual isocyanate detectable (determined via FT-IR, limit of residual NCO is less than 0.05 as signal height of the NCO band at 2273 cm$^{-1}$). Completion of the reaction is typically achieved after stirring for 16 to 24 hours at a temperature of about 50° C. unless stated otherwise. The product can be used without further purification.

Synthesis of Monomers Via the Sn-Catalyzed Addition of Hydroxyl Groups onto the Isocyanate Group of IEM Example 1

According to the General Procedure A 44.6 g of IEM was added to 50.0 g of 2,2-Bis[4-(3-hydroxypropyloxy)-phenyl]propane containing 500 ppm of dibutyltindilaureate (DBTDL, with respect to the total amount of the educts). 94.8 g of 2,2-Bis{4-[3-(N-2-methacroyloxyethyl)-carbamoyloxypropyloxy]-phenyl}propane (P-IEM) were isolated as viscous oil (η=460 Pa*s, $n_D^{20}$=1.5356).

Example 2

According to the General Procedure A 46.1 g of IEM was added to 60.7 g of ethoxylated bisphenol A (about 2 EO per phenol, Seppic Dianol 240) containing 500 ppm of DBTDL. 107 g of (idealized) 2,2-Bis{4-(2-[2-(N-2-methacroyloxyethyl)-carbamoyloxyethyloxy]-ethyloxy)-phenyl}propane (D-IEM) were isolated as viscous oil (η=165 Pa*s, $n_D^{20}$=1.5323).

Example 3

According to the General Procedure A 35.3 g of IEM was added to 46.0 g of 2,2-Bis[3,5-dimethyl-4-(3-hydroxypropyloxy)-phenyl]propane (TMP alcohol containing 500 ppm of DBTDL). 81.6 g of 2,2-Bis{3,5-dimethyl-4-[3-(N-2-methacroyloxyethyl)-carbamoyloxy-propyloxy]-phenyl}propane (TMP-IEM) were isolated as viscous oil (η>750 Pa*s, $n_D^{20}$=1.5302).

Example 4

According to the General Procedure A 29.8 g of IEM was added to 46.8 g of 2,2-Bis[3,5-dichloro-4-(3-hydroxypropyloxy)-phenyl]propane (TCP alcohol) containing 500 ppm of DBTDL. 76.9 g of 2,2-Bis{3,5-dichloro-4-[3-(N-2-methacroyloxyethyl)-carbamoyloxy-propyloxy]-phenyl}propane (TCP-IEM) were isolated as viscous oil (η=400 Pa*s, $n_D^{20}$=1.5391).

Example 5

According to the General Procedure A 34.8 g of IEM was added to 51.3 g of 1,1,1,3,3,3-Hexafluoro-2,2-bis[4-(3-hydroxypropyloxy)-phenyl]propane (HFP alcohol) containing 500 ppm of DBTDL. 86.4 g of 1,1,1,3,3,3-Hexafluoro-2,2-bis{4-[3-(N-2-methacroyloxyethyl)-carbamoyloxypropyloxy]-phenyl}propane (HFP-IEM) were isolated as viscous oil (η>750 Pa*s, $n_D^{20}$=1.5095).

Comparative Example 1

According to the General Procedure A 31.0 g of IEM was added to 51.3 g of Bis-GMA containing 500 ppm of DBTDL. 82.3 g of Bis-GMA diurethane dimethacrylate (BUM) were isolated as viscous oil (η=1060 Pa*s, $n_D^{20}$=1.5267).

Synthesis of Monomers Via the Bi-Catalyzed Addition of Hydroxyl Groups onto the Isocyanate Group of IEM Example 6

According to the General Procedure A 46.1 g of IEM was added to 60.7 g of ethoxylated bisphenol A (about 2 ethoxy (EO) groups per phenol, Seppic Dianol 240) containing 100 ppm of Bi with respect to the total amount of the educts (bismuth 20 wt.-% neodecanoate, Shepherd BICAT 8108M). 107 g of (idealized) 2,2-Bis{4-(2-[2-(N-2-methacroyloxyethyl)-carbamoyloxyethyloxy]-ethyloxy)-phenyl}propane (D-IEM) were isolated as viscous oil (η=165 Pa*s, $n_D^{20}$=1.5326).

Example 7

According to the General Procedure A 46.1 g of IEM was added to 76.5 g of ethoxylated bisphenol A (about 3.25 EO per phenol, Seppic Dianol 265) containing 100 ppm of Bi. 123 g of the corresponding dimethacrylate compound (D2-IEM) were isolated as viscous oil (η=36 Pa*s, $n_D^{20}$=1.5257).

Example 8

According to the General Procedure A 39.9 g of IEM was added to 77.6 g of ethoxylated bisphenol A (about 4.25 EO groups per phenol, Seppic Dianol 285) containing 100 ppm of Bi. 118 g of corresponding dimethacrylate compound (D3-IEM) were isolated as viscous oil (η=15 Pa*s, $n_D^{20}$=1.5197).

Example 9

According to the General Procedure A 46.1 g of IEM was added to 66.3 g of propoxylated bisphenol A (about 2 propyloxy (PO) groups per phenol, Seppic Dianol 340) containing 100 ppm of Bi. 113 g of corresponding dimethacrylate compound (D5-IEM) were isolated as viscous oil (η=750 Pa*s, $n_D^{20}$=1.5214).

Example 10

According to the General Procedure A 71.1 g of IEM was added to 80.0 g of ethoxylated bisphenol A (about 2 EO groups per phenol, Seppic Dianol 240) and 20.0 g of ethoxylated bisphenol A (about 4.25 EO groups per phenol, Seppic Dianol 285) containing 100 ppm of Bi. 170 g of the mixture of corresponding dimethacrylate compounds (D-IEM:D3-IEM=80:20 by weight) were isolated as viscous oil ($\eta$=119 Pa*s, $n_D^{20}$=1.5309).

Synthesis of Monomers Via the Non-Catalyzed Addition of Hydroxyl Groups onto the Isocyanate Group of IEM Example 11

According to the General Procedure A 46.1 g of IEM was added to 60.7 g of ethoxylated bisphenol A (about 2 EO groups per phenol, Seppic Dianol 240). After stirring 96 hours at 60° C. 107 g of (idealized) 2,2-Bis{4-(2-[2-(N-2-methacroyloxyethyl)-carbamoyloxyethyloxy]-ethyloxy)-phenyl}propane (D-IEM) were isolated as viscous oil ($\eta$=183 Pa*s, $n_D^{20}$=1.5330).

Comparative Example 2

According to the General Procedure A 78.0 g of IEM was added to 51.0 g of Tricyclodecandimethanol (TCD alcohol DM). 129 g of TCD alcohol-IEM (T-IEM) were isolated as viscous oil ($\eta$=390 Pa*s, $n_D^{20}$=1.5099).

The dental compositions listed in Table 2 below were prepared according to General Procedure B.

General Procedure B:

With magnetic stirring and under the exclusion of light the initiator system components were dissolved within the monomers at temperatures not above 50° C. (depending on the intrinsic viscosity of the used monomers). The obtained dental composition was then light cured using a 800 mW halogen curing light (3M ESPE Elipar™ Trilight) and tested according to the corresponding measurements listed above.

Some of the monomers were tested with respect to mechanical properties and to shrinkage behaviour. The content of the composition tested and the test results are given in Table 2 below.

TABLE 2

| | Dental Composition | | | | |
|---|---|---|---|---|---|
| | I | II | III | IV | V |
| a | 98.2 | | | | |
| b | | 98.2 | 49.1 | 78.6 | |
| c | | | 49.1 | | |
| d | | | | 19.6 | |
| e | | | | | 98.2 |
| f | 0.17 | 0.17 | 0.17 | 0.17 | 0.17 |
| g | 1.00 | 1.00 | 1.00 | 1.00 | 1.00 |
| h | 0.60 | 0.60 | 0.60 | 0.60 | 0.60 |
| FS(I) | 102 ± 3.00 | 106 ± 4.00 | 101 ± 2.00 | 103 ± 6.00 | 97.0 ± 5.00 |
| E-M(I) | 1.99 ± 0.10 | 2.12 ± 0.10 | 2.14 ± 0.06 | 2.23 ± 0.16 | 1.83 ± 0.05 |
| VC | 4.82 ± 0.06 | 5.16 ± 0.06 | 4.97 ± 0.04 | 5.20 ± 0.07 | 5.98 ± 0.05 |

The dental compositions listed in Tables 3 and 4 below were prepared according to General Procedure C.

General Procedure C

According to General Procedure B the initiator system components were dissolved within the monomers. Under the exclusion of light and using a two-arm kneader the filler was mixed in portions with this mixture of initiator system and monomers. The amount of filler was manually determined depending on the desired handling properties of the dental composition. The dental composition was then light cured using a 800 mW halogen curing light (3M ESPE Elipar™ Trilight) and tested according to the corresponding measurements listed above. The respective values are given in Tables 3 and 4.

TABLE 3

Compositions Containing Inventive and Comparative Examples and Data of the Cured Compositions

| | Dental Composition | | | | | | | |
|---|---|---|---|---|---|---|---|---|
| | A | B | C | D | E | F | G | H |
| a | 7.22 | 6.43 | | 14.2 | | | | |
| b | | | | | | | 18.3 | 14.6 |
| c | | | | | 18.3 | | | |
| d | | | | | | 18.4 | | 3.69 |
| e | | | | | | | | |
| f | 0.03 | 0.03 | 0.03 | 0.03 | 0.03 | 0.03 | 0.03 | 0.03 |
| g | 0.18 | 0.17 | 0.18 | 0.17 | 0.19 | 0.19 | 0.19 | 0.19 |
| h | 0.09 | 0.09 | 0.09 | 0.09 | 0.09 | 0.09 | 0.09 | 0.09 |
| i | 7.83 | | | | | | | |
| j | | 7.78 | | | | | | |

TABLE 3-continued

Compositions Containing Inventive and Comparative Examples and Data of the Cured Compositions

| | Dental Composition | | | | | | | |
|---|---|---|---|---|---|---|---|---|
| | A | B | C | D | E | F | G | H |
| k | | | 15.1 | | | | | |
| m | | | | | | | | |
| n | | | | | | | | |
| o | | | | | | | | |
| p | | | | | | | | |
| q | 2.65 | 2.50 | 2.60 | 2.51 | | | | |
| r | | | | | | | | |
| s | 82.0 | 83.0 | 82.0 | 83.0 | 81.4 | 81.3 | 81.4 | 81.4 |
| CS | 393 ± 26.0 | 333 ± 94.0 | 403 ± 58.0 | 404 ± 26.0 | 343 ± 40.0 | 353 ± 38.0 | 368 ± 25.0 | 406 ± 14.0 |
| FS(I) | 157 ± 9.00 | 162 ± 13.0 | 156 ± 16.0 | 168 ± 19.0 | 112 ± 12.0 | 69.0 ± 5.00 | 162 ± 12.0 | 147 ± 24.0 |
| FS(II) | | | | 138 ± 22 | | | | 113 ± 5.00 |
| E-M(I) | 12.8 ± 0.50 | 14.6 ± 0.70 | 14.1 ± 0.70 | 13.2 ± 0.40 | 7.10 ± 0.40 | 2.20 ± 0.10 | 12.1 ± 0.40 | 11.3 ± 0.60 |
| E-M(II) | | | | 13.3 ± 0.70 | | | | 10.1 ± 0.30 |
| TBWR | 1.01 ± 0.12 | 1.11 ± 0.14 | 1.06 ± 0.10 | 0.87 ± 0.11 | 1.48 ± 0.22 | | 1.00 ± 0.12 | 1.15 ± 0.13 |
| SHR | 1.50 ± 0.01 | 1.50 ± 0.02 | 1.47 ± 0.02 | 1.51 ± 0.01 | 1.51 ± 0.03 | 1.53 ± 0.02 | 1.36 ± 0.03 | 1.36 ± 0.03 |

TABLE 4

| | Dental Composition | | | | | | | |
|---|---|---|---|---|---|---|---|---|
| | I | J | K | L | M | N | O | P |
| a | | | 12.8 | | | | | |
| b | 14.6 | 14.6 | | | | | | |
| c | | | | | | | | |
| d | | | | | | | | |
| e | | | | 12.8 | | | | |
| f | 0.03 | 0.03 | 0.03 | 0.03 | 0.03 | 0.03 | 0.03 | 0.03 |
| g | 0.19 | 0.19 | 0.19 | 0.19 | 0.19 | 0.18 | 0.18 | 0.18 |
| h | 0.09 | 0.09 | 0.09 | 0.09 | 0.09 | 0.09 | 0.09 | 0.09 |
| i | | | | | | | | |
| j | | | | | | | | |
| k | | | | | | | | |
| l | | | | | | | | |
| m | | | | | 12.8 | | | |
| n | | | | | | | | 9.15 |
| o | 3.69 | | | | | 9.15 | | |
| p | | | | | | 9.15 | | |
| q | | | | | 5.49 | | 9.15 | |
| r | | 3.69 | 5.49 | 5.49 | | | | 17.7 |
| s | 81.4 | 81.4 | 81.4 | 81.4 | 81.4 | 81.4 | 81.4 | 82.0 |
| CS | 397 ± 25.0 | 423 ± 22.0 | 412 ± 12.0 | 378 ± 68.0 | 489 ± 39.0 | 424 ± 71.0 | 461 ± 56.0 | 424 ± 9.00 |
| FS(I) | 167 ± 20.0 | 168 ± 10.0 | 164 ± 12.0 | 170 ± 15.0 | 143 ± 25.0 | 153 ± 26.0 | 141 ± 17.0 | 137 ± 18.0 |
| FS(II) | 142 ± 20.0 | 118 ± 14.0 | 172 ± 36.0 | | | 144 ± 20.0 | 111 ± 8 | |
| E-M(I) | 12.0 ± 0.30 | 11.7 ± 0.20 | 11.9 ± 0.50 | 12.2 ± 0.40 | 12.8 ± 0.80 | 13.5 ± 0.60 | 14.5 ± 0.40 | 11.7 ± 0.20 |
| E-M(II) | 11.5 ± 0.40 | 11.6 ± 0.40 | 12.5 1.5 | | | 13.5 ± 0.20 | 14.1 ± 0.20 | |
| TBWR | | 0.98 ± 0.12 | | | | 0.78 ± 0.08 | 0.81 ± 0.08 | |
| SHR | 1.48 ± 0.01 | 1.47 ± 0.03 | 1.44 ± 0.03 | 1.54 ± 0.02 | 1.93 ± 0.01 | 2.04 ± 0.09 | 2.31 ± 0.01 | 1.82 ± 0.03 |

The invention claimed is:

1. A dental composition comprising:
   a) a resin matrix comprising hardenable components, the resin matrix comprising at least about 10 wt.-% of the whole composition,
   b) a filler matrix, the filler matrix comprising at least about 30 wt.-% of the whole composition,
   c) an initiator being able to start the hardening process of the hardenable components being present in the resin matrix,
   d) optionally further additives selected from the group consisting of pigments, colourants, stabilizers, retarders, plasticizers, flavourants, anti-microbials, fragrance, agents that impart fluorescence and/or opalescence and fluoride releasing materials and mixtures thereof;
   wherein the resin matrix comprises the monomer or mixture of monomers represented by the following structure

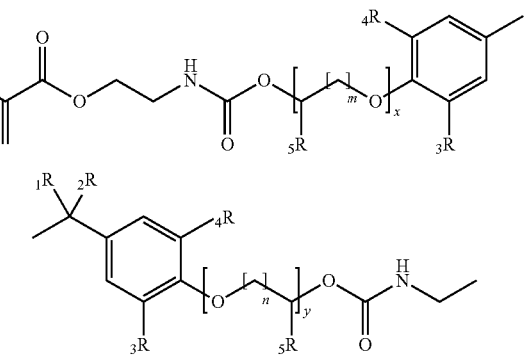

(1)

-continued

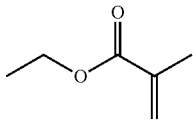

with $R_1, R_2$ independently selected from H, alkyl, and Phenyl,
$R_3, R_4$ independently selected from H and alkyl and halogen,
$R_5$ independently selected from H and alkyl,
where m=n=2 and x+y=2.

2. The dental composition according to claim 1 fulfilling at least one of the following parameters after hardening:
Compressive Strength (MPa): at least about 320, determined according to ISO 9917 using cubic specimen (dimensions 3 mm×3 mm×5 mm),
Flexural Strength (MPa): at least about 120, determined according to ISO 4049,
E-Modulus (GPa): at least about 9, determined according to ISO 4049 and/or
Bonded Disk Shrinkage-Strain (vol.-%): less or equal than about 1.6, determined according to the Watts protocol.

3. The dental composition according to claim 1, wherein the filler matrix comprises filler(s) having an average particle diameter of less than about 200 nm and mixtures thereof.

4. The dental composition according to claim 1, wherein the resin matrix comprises at least one hardenable component being different from the monomers or mixtures of monomers according to claims 1 to 3 and having free radically active functional groups.

5. The dental composition according to claim 1, wherein the initiator is selected from systems which initiate polymerization via radiation, heat, or a redox reaction or a mixture of those systems.

6. The dental composition according to claim 1, comprising:
the resin matrix in an amount of about 10 to about 50 wt.-%,
the filler matrix in an amount of about 30 to about 85 wt.-%,
the initiator in an amount of about 0.1 to about 3 wt.-%,
optionally additives in an amount of about 0 to about 25 wt.-%, wt.-% with respect to the whole composition.

7. The dental composition according to claim 1 that is any of casting materials, cements, coating compositions or sealants.

8. The dental composition according to claim 1 being stored in a container, the container having the shape of a compule or a dual-chamber cartridge.

9. A method for the production of a dental composition to be used in a process comprising the steps of:
a) providing a dental composition according to claim 1;
b) placing the dental composition comprising the monomer or mixture of monomers in contact with a tooth; and
c) hardening the composition.

10. The dental composition according to claim 1 that, upon hardening, is any of artificial crowns, anterior or posterior fillings, cavity liners, mill blanks, orthodontic devices, restoratives, or prostheses.

* * * * *

UNITED STATES PATENT AND TRADEMARK OFFICE
CERTIFICATE OF CORRECTION

PATENT NO. : 8,426,490 B2
APPLICATION NO. : 12/679490
DATED : April 23, 2013
INVENTOR(S) : Peter Bissinger It is certified that error appears in the above-identified patent and that said Letters Patent is hereby corrected as shown below:

On the Title Page, in Column 2, under "(Other Publications)"
Line 1, delete "Volumne" and insert -- Volume --, therefor.

On Title Page 2, in Column 2, under "(Other Publications)"
Line 43, delete "Februrary" and insert -- February --, therefor.

In the Specifications:

Column 5
Line 39, delete "i.a." and insert -- i.e. --, therefor.

Column 9
Line 41, delete "dibutyl tindilaurate" and insert -- dibutyltin dilaurate --, therefor.

Column 10
Line 30, delete "tetrahydrofurane" and insert -- tetrahydrofuran --, therefor.

Column 11
Line 22, delete "Pyconmeter" and insert -- Pycnometer --, therefor.
Line 22, delete "Micrometritics" and insert -- Micromeritics --, therefor.

Column 16
Line 28, delete "componentsor" and insert -- components or --, therefor.

Column 19
Lines 46-47, delete "quarternary" and insert -- quaternary --, therefor.

Column 20
Lines 25-26, delete "(lithopones)," and insert -- (lithophones), --, therefor.

Signed and Sealed this
Twenty-seventh Day of August, 2013

Teresa Stanek Rea
*Acting Director of the United States Patent and Trademark Office*